United States Patent [19]

Firth et al.

[11] 4,447,657

[45] May 8, 1984

[54] PREPARATION OF ORTHO-ALKYLATED PHENOLS

[75] Inventors: Bruce E. Firth, Arlington Heights, Ill.; Terry J. Rosen, Berkeley, Calif.

[73] Assignee: UOP Inc., Des Plaines, Ill.

[21] Appl. No.: 440,676

[22] Filed: Nov. 10, 1982

[51] Int. Cl.$^3$ .................. C07C 37/05; C07C 39/06
[52] U.S. Cl. ................................................. 568/783
[58] Field of Search ........................................ 568/783

[56] References Cited

U.S. PATENT DOCUMENTS 2,289,886 7/1942 Schmerling ..................... 568/783
2,551,628 5/1951 Nickel ............................... 568/783
4,283,572 8/1981 Klicker ............................. 568/783

FOREIGN PATENT DOCUMENTS 2345911 3/1975 Fed. Rep. of Germany ...... 568/783

OTHER PUBLICATIONS

Dewar et al. "Jour. Chem. Soc." (1959) pp. 4080–4095.
Dewar et al. "Jour. Chem. Soc." (1960) pp. 459–963.

Primary Examiner—Werren B. Lone
Attorney, Agent, or Firm—James R. Hoatson, Jr.; Eugene I. Snyder; William H. Page, II

[57] ABSTRACT

Alkyl phenyl ethers may be induced to undergo thermal rearrangement on an alumina catalyst to afford the isomeric ortho-alkylphenol. Such rearrangement generally occurs under milder conditions than does the alkylation of a phenol with an olefin using the same alumina as an alkylating catalyst. Yields frequently are high with good selectivity.

13 Claims, No Drawings

PREPARATION OF ORTHO-ALKYLATED PHENOLS

Alkylphenols are materials of commerce desirable for their antioxidant properties. Many members of this class have commercial utility in such applications as antioxidants and stabilizing agents for fuel oils and antioxidants for foods of diverse type. Among the phenols which are antioxidants the ortho-alkyl- and ortho, ortho dialkyl-phenols appear to be superior. That is to say, the ortho-alkylphenols and ortho, ortho-dialkylphenols seem to be better antioxidants than their isomers. There is a corresponding need to prepare such ortho-alkylated phenols with relatively high selectivity and yield.

The usual method of preparing alkylphenols is to alkylate phenols with an olefin, alkyl halide, or alcohol in the presence of an alkylating catalyst which generally is a Lewis acid. Catalysts which have been employed include strong inorganic acids (sulfuric acid, phosphoric acid, and hydrofluoric acid to name a few), strong organic acids (for example, sulfonic acids and cationic exchange resins bearing such acid functionalities), metal halides (boron trifluoride, aluminum halides, and zinc halides are exemplary) and inorganic oxides such as alumina and silica. A deficiency in all such methods is their limited selectivity for ortho-alkylation, that is, alkylation at available ortho positions occurs with only limited preference to alkylation at other available positions. Another limitation in such methods is that some 2,4-dialkylphenols undergo further alkylation to 2,4,6-trialkylphenols only with great difficulty, if at all. Still another disadvantage is the relatively high reaction temperature necessary where the more selective alkylating catalysts are used, for example, inorganic oxides.

Some instances of the rearrangement of alkyl phenyl ethers to the isomeric alkylphenol have been reported. For example, U.S. Pat. No. 2,289,886 discloses that alkyl phenyl ethers when treated with hydrogen fluoride afford both the isomeric alkylphenol and the dealkylated phenol. More recently U.S. Pat. No. 4,283,572 describes the rearrangement of nonyl phenyl ether to a mixture of phenol, mononoylphenol, and dinonyl-phenol. Such sparse reports are in marked contrast to the well-known thermal rearrangement of allyl phenyl ethers to allyl phenols (Claisen rearrangement) where the allyl group migrates selectively to an ortho or, less often, to a para position.

We have made the remarkable discovery that alkyl phenyl ethers undergo a thermal rearrangement in the presence of an alumina as catalyst to afford the isomeric ortho-alkylphenols with high yield and good selectivity. Not only is the thermal rearrangement of an alkyl phenyl ether to an alkylphenol as a general phenomenon without precedent, but the regioselectivity of the rearrangement to afford an ortho- alkylphenol is completely surprising.

Such a method of ortho-alkylating phenols has many advantages over the prior art methods. One advantage is formation of the ortho-alkylphenol at a substantially lower temperature than was previously possible. That is to say, the rearrangement occurs at a temperature lower than that necessary for alkylation of the phenol with, for example, an olefin using an alumina as the alkylating catalyst. Since the alkyl phenyl ether may be prepared from a phenol under relatively mild conditions, our discovery makes possible a two-stage preparation of an alkylphenol via (1) formation of alkyl phenyl ether followed by (2) rearrangement of the ether, both reactions proceeding under substantially milder conditions than direct alkylation of the phenol.

Another advantage of the invention described herein is its great selectivity in affording ortho-alkylated phenols. Thus, the prior art alkylating methods afford ortho-alkylated materials with varying selectivity, whereas the method we describe below affords ortho-alkylated produced with substantially improved selectivity.

Still another advantage of the method which is our invention is that it affords products which sometimes are not otherwise readily available. For example, ethers of an (2-alkylphenyl) alkyl ether undergo rearrangement to the isomeric 2,6-dialkylphenol with great specificity, whereas direct alkylation of the same 2-alkylphenol may fail to afford the desired 2,6-dialkylphenol, or do so only in relatively poor yield.

SUMMARY OF THE INVENTION

An object of the invention described herein is to prepare ortho-alkylphenols by rearrangement of the isomeric alkyl phenyl ethers. One embodiment is a method of rearrangement which is thermally induced on an alumina catalyst. In a more specific embodiment the catalyst is a fluorided alumina and the temperature is from about 75° to about 200° C.

Another object of our invention is to alkylate phenols selectively at the ortho position by converting the phenol to an alkyl phenyl ether and rearranging the latter in a thermal reaction on an alumina catalyst. In a specific embodiment the reactant phenol is a 2-alkylphenol and the product is a 2,6-dialkylphenol.

DESCRIPTION OF THE INVENTION

In one aspect the invention described herein is a method of rearranging an alkyl phenyl ether to an isomeric ortho-alkylphenol comprising heating said ether in contact with an alumina under rearrangement conditions and recovering the ortho-alkylphenol. In another aspect our invention is a method of ortho-alkylating a phenol comprising converting the phenol to an alkyl phenyl ether, thermally rearranging the ether in the presence of an alumina catalyst, and recovering the formed ortho-alkylphenol.

We have found that alkyl phenol ethers can be induced to undergo thermal rearrangement in contact with an alumina. The alkyl group may be an unsubstituted alkyl, i.e., $C_nH_{2n+1}$, or it may be a substituted alkyl group where the substituent is otherwise inert under the reaction conditions. Examples of inert substituents include the halogens, a substituted or unsubstituted amino group, an aryl moiety, esters, the nitro group, and so forth. In this specification it is to be understood that the term "alkyl" refers both to unsubstituted and substituted alkyl groups.

Secondary and tertiary alkyl groups are preferred. Except for benzyl and similar arylmethyl groups, primary alkyl groups rearrange with difficulty, often with isomerization of the alkyl group itself, thereby limiting their utility in this invention. Examples of suitable alkyl groups include propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, benzyl, and so forth.

The aromatic portion of the alkyl phenyl ethers of this invention may be the unsubstituted phenyl group itself, but in the more usual case the aromatic ring contains one or more groups which are otherwise inert, subject to the provision that at least one ortho position remains unsubstituted. Examples of inert ring substituents include the halogens, and the nitro, ester, and alkyl groups. Alkyl substituents are especially important, and the ring substituted alkyl group may be the same or different from the alkyl portion of the ether. The alkyl group may occupy any of the ring positions, but 2-alkyl phenyl ethers are especially desirable reactants. The most desirable ring-substituted alkyl groups are those containing up to about 10 carbon atoms. Examples include methyl, ethyl, propyl, butyl, pentyl, hexyl, heptyl, octyl, nonyl, and decyl groups. Illustrative examples of the aromatic portion of the alkyl phenyl ethers of this invention include 2-methylphenyl, 3-methylphenyl, 4-methylphenyl, 2,4-dimethylphenyl, 2-ethylphenyl, 4-ethylphenyl, 2-n-propylphenyl, 3-n-propylphenyl, 2-i-propylphenyl, 4-i-propylphenyl, 2,4-i-propylphenyl, 2-i-propyl-4-methylphenyl, 2-t-butylphenyl, 2-t-butylphenyl, 4-t-butylphenyl, 2-t-butyl-4-methylphenyl, 2-methyl-4-t-butylphenyl, the isomeric pentylphenyls, hexylphenyls, heptphenyls, and so on.

The alkyl phenyl ethers of this invention are caused to undergo a thermally induced rearrangement in contact with an alumina. Although any alumina will suffice, those aluminas whose acidity has been enhanced are preferred. One such group of aluminas are halided aluminas, especially chlorided and fluorided alumina, and particularly fluorided alumina. Fluorided alumina, for example, which is the product wherein fluoride ions have been deposited in the alumina matrix, may be prepared by contacting alumina with a solution of ammonium fluoride, evaporating the water while mixing, and calcining the resultant product. Another mode of preparation, by way of illustration, is passage of gaseous hydrogen fluoride over solid alumina, wherein the contact time and the total amount of hydrogen fluoride to which the alumina is exposed will determine the final fluoride content of the product.

The efficacy of the halided alumina catalyst in inducing thermal rearrangement depends upon the halide content of the catalyst. Preparations containing from about 0.3 to about 5 wt. % halide are preferred, and those from about 0.3 to about 3 wt. % halide are especially preferred.

Where the rearrangement occurs with particular facility, an alumina whose acidity has been decreased may be advantageous. One such group of aluminas are those containing alkali metal cations, especially lithium, in the alumina matrix. Where lithiated alumina is used for alkyl phenyl ethers particularly prone to rearrangement, little isomerization of the ortho-alkylated product occurs subsequent to formation. Lithiated alumina containing from about 0.3 to about 5 wt. % lithium is preferred, with those from about 0.5 to about 3% being especially preferred.

Silica-alumina containing up to about 75% silica may also be used as a catalyst in this invention. Some silica-aluminas, being substantially more acidic than, for example, fluorided alumina, are somewhat less efficaceous than the latter in the selectivity of the rearrangement to ortho-alkylated product. A halided silica-alumina also may be used in the practice of this invention.

The amount of alumina used in the practice of this invention depends upon the nature of the alkyl group, that is, whether primary, secondary, or tertiary, and the rate of rearrangement desired. When the reaction is run in a batch mode the amount of alumina used may vary from about 0.1 to over 100% by weight relative to the ether to be rearranged.

The ether is contacted with an alumina under rearrangement conditions. The temperature at which rearrangement occurs may be from about 75° C. to about 200° C. depending upon the nature of the alkyl group. It has been found that a tertiary group undergoes rearrangement substantially more readily than does a secondary alkyl group, which in turn rearranges more readily than does a primary alkyl group. Thus, the reaction temperature is lowest for a tertiary alkyl group undergoing rearrangement and highest when a primary alkyl group undergoes rearrangement. Where a secondary alkyl group undergoes rearrangement a temperature from about 140° to about 175° C. generally suffices.

Since pressure has no important effect on this reaction rearrangement generally is performed under autogeneous pressure.

Conversion of phenols to alkyl phenyl ethers may be performed by any method known in the art. For example, the phenol can be converted to its phenoxide which is then reacted with an alkyl halide, often in a relatively polar solvent. Another example of a preparative route is the reaction of a phenol with an alcohol in the presence of an acid catalyst, such as a strong inorganic acid or a cationic exchange resin bearing sulfonic acid groups. Still another preparative route is the reaction of a phenol with an olefin in the presence of a Lewis acid, such as an inorganic oxide as alumina or a metal halide. It is to be understood that the conversion of a phenol to its alkyl phenyl ether is well known in the art and need not be described here in any great detail.

The following examples are illustrative of this invention and are not to be construed as limiting the invention thereto.

EXAMPLE 1

To 15 g of isopropyl (2-isopropylphenyl) ether was added 8 g of 1% fluorided alumina. The mixture was placed in a 300 cc stirred autoclave and the system was flushed with nitrogen and left under a nitrogen atmosphere. The autoclave was heated to 150° C. for 1 hour with stirring during which time the pressure reached 200 psig. The cooled reaction mixture was taken up in acetone, filtered, and the solvent was removed on a rotary evaporator. The residue was analyzed by gas-liquid phase chromatography (glpc) which showed the presence of 2-isopropylphenol (10%), isopropyl(2-isopropylphenyl) ether (28%), 2,6-diisopropylphenol (60%), and 2,4,6-triisopropylphenol (2%). Thus, the 2,6-diisopropylphenol was formed with 83% selectivity.

EXAMPLE 2

A mixture of 11.4 g of 2-isopropylphenol and 8 g of 1% fluorided alumina in a 300 cc stirred autoclave was reacted with 3.5 g propylene (84 mmol) at 155° C. for 1 hour. The reaction mixture was processed as described above and analyzed by glpc, which showed only a trace of 2,6-diisopropylphenol.

Two conclusions may be drawn from this result when compared to that of the prior example. One is that the isopropyl ether of the phenol rearranges under conditions where isopropylation of 2-isopropylphenol does not occur. The second conclusion which may be drawn is that rearrangement of the ether occurs by a route different from disproportionation of the ether to a phenol and an olefin followed by subsequent alkylation of the phenol by the olefin.

EXAMPLE 3

A mixture of 15 g of isopropyl (4-isopropylphenyl) ether and 8 g of 1% fluorided alumina in a stirred autoclave was heated under nitrogen to 160° C. for 1 hour. After processing as described in Example 1, analysis by glpc showed the reaction mixture consisted of 4-isopropylphenol and/or isopropyl (4-isopropylphenyl) ether (41%), 2,4-diisopropylphenol (43%), and 2,4,6-triisopropylphenol (12%). Assuming the first named product was largely, or exclusively, the ether, the latter two products were formed with a selectivity of 73 and 20%, respectively.

EXAMPLE 4

Experiment 1 was repeated using 4 g of a 1:1 silica-alumina catalyst. After 1 hour at 150°-165° C. glpc showed the product distribution to be 2-isopropylphenol (19%), 2,6-diisopropylphenol (39%), 2,4-diisopropylphenol (15%), 2,4,6-triisopropylphenol (23%), and 2,5-diisopropylphenol (2%).

EXAMPLE 5

A solution of 2-isopropylphenol (75 g, 0.54 mol) in 60 ml methanol was added, under nitrogen, to a solution of sodium methoxide, prepared by reacting 13.1 g (0.57 mol) sodium with 150 ml dry methanol. To this stirred solution was added isopropyl bromide (82.2 g, 0.66 mol) dropwise over several hours, after which the reaction mixture was heated at reflux overnight. The cooled mixture was filtered to remove solids and methanol was removed on a rotary evaporator. The residue, containing both liquid and solid, was treated with about equal volumes of diethyl ether and water, with the aqueous phase then separated and discarded. The ether phase was washed with Claisen solution, water being added to facilitate separation of phases, and the organic phase retained. The combined aqueous phases was extracted with ether, the extract being added to the prior retained organic phase, and the combined material was dried over anhydrous magnesium sulfate. Ether was removed by evaporation and the residue was distilled to afford isopropyl (2-isopropylphenyl) ether.

A portion of the distillate was contacted with 1% fluorided alumina at 150°-160° C. as described in Example 1. The product mixture obtained after rearrangement afforded 2,6-diisopropylphenol in an overall yield of 35% based on 2-isopropylphenol.

What is claimed is:

1. A method of rearranging a secondary alkyl or tertiary alkyl phenyl ether to an ortho-alkylphenol comprising contacting said ether with an alumina selected from the group consisting of halided aluminas, aluminas containing an alkali metal cation in the matrix, and silica-alumina containing up to about 75% silica, at a temperature from about 75° C. to about 175° C. and recovering the ortho-alkyl phenol.

2. The method of claim 1 where both ortho-positions of the aromatic ring in the ether are occupied by hydrogen.

3. The method of claim 1 wherein the ether is a (2-alkylphenyl) alkyl ether.

4. The method of claim 1 wherein the alumina is a fluorided alumina.

5. The method of claim 1 where the alumina is a lithiated alumina.

6. The method of claim 1 where the ether is an isopropyl ether.

7. The method of claim 1 where the ether is a tertiary butyl ether.

8. A method of ortho-alkylating a phenol comprising converting the phenol to an alkyl phenyl ether, where said alkyl is a secondary or tertiary alkyl moiety, thermally rearranging the ether in the presence of an alumina catalyst at a temperature from about 75° C. to about 175° C., where the alumina is a halided alumina, an alumina containing an alkali metal cation in the matrix, or a silica-alumina containing up to about 75% silica, and recovering the formed ortho-alkylphenol.

9. The method of claim 8 where the phenol is a 2-alkylphenol.

10. The method of claim 8 where the alumina is a fluorided alumina.

11. The method of claim 8 where the alumina is a lithiated alumina.

12. The method of claim 8 where the ether is an isopropyl ether.

13. The method of claim 8 where the ether is a tertiary butyl ether.

* * * * *